United States Patent
Botton et al.

(10) Patent No.: US 9,233,937 B2
(45) Date of Patent: *Jan. 12, 2016

(54) METHOD OF STIMULATING INSULIN SECRETION AND/OR MODULATING INS-1 KINASE WITH SUBSTITUTED PYRAZINONES AND/OR SUBSTITUTED TETRAHYDROQUINOXALINONES

(71) Applicant: MERCK PATENT GMBH, Darmstadt (FR)

(72) Inventors: Gerard Botton, Buc (FR); Eric Valeur, Bretigny sur Orge (FR); Christine Charon, Gometz-le-Chatel (FR); Micheline Kergoat, Bures-sur-Yvette (FR); Samer Elbawab, Bures-sur-Yvette (FR)

(73) Assignee: MERCK PATENT GMBH, Darmstadt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,796

(22) Filed: Jul. 22, 2014

(65) Prior Publication Data

US 2014/0329837 A1 Nov. 6, 2014

Related U.S. Application Data

(62) Division of application No. 12/990,098, filed as application No. PCT/EP2009/002328 on Mar. 31, 2009, now Pat. No. 8,815,859.

(30) Foreign Application Priority Data

Apr. 29, 2008 (EP) .................... 08008165

(51) Int. Cl.
| | |
|---|---|
| *C07D 241/18* | (2006.01) |
| *C07D 241/44* | (2006.01) |
| *C07D 241/08* | (2006.01) |
| *C07D 241/38* | (2006.01) |
| *C07D 401/04* | (2006.01) |
| *C07D 403/04* | (2006.01) |
| *C07D 405/04* | (2006.01) |

(52) U.S. Cl.
CPC ............ *C07D 241/08* (2013.01); *C07D 241/18* (2013.01); *C07D 241/38* (2013.01); *C07D 401/04* (2013.01); *C07D 403/04* (2013.01); *C07D 405/04* (2013.01)

(58) Field of Classification Search
CPC ............................ C07D 241/18; C07D 241/44
USPC ................... 544/354, 408; 546/152; 548/469; 549/434
See application file for complete search history.

(56) References Cited

U.S. PATENT DOCUMENTS

| | | | |
|---|---|---|---|
| 4,837,319 | A | 6/1989 | Yaso et al. |
| 4,877,875 | A | 10/1989 | Yaso et al. |
| 4,877,877 | A | 10/1989 | Yaso et al. |
| 7,182,791 | B2 | 2/2007 | Plos et al. |
| 2004/0063693 | A1 | 4/2004 | Cernerud et al. |
| 2008/0280873 | A1 | 11/2008 | Liang et al. |
| 2009/0012062 | A1 | 1/2009 | Andres-Gil et al. |

FOREIGN PATENT DOCUMENTS

| | | |
|---|---|---|
| EP | 0 242 957 | 10/1987 |
| WO | WO-02 092090 | 11/2002 |
| WO | WO-2004 009586 | 1/2004 |
| WO | WO-2005 097136 | 10/2005 |
| WO | WO-2007 071646 | 6/2007 |
| WO | WO-2007149448 | 12/2007 |

OTHER PUBLICATIONS

Azzam, R. et al., "Expanding the substitution pattern of 2(1H)-pyrazinones via Suzuki and Heck reactions," Tetrahedron, 2005, vol. 61, pp. 3953-3962.
Bergman, J. et al., "Synthesis of 5H-Pyrazino[2,3-b]indoles from Indoles-2,3-dione Derivatives," Acta Chemica Scandinavica, 1997, vol. 51, pp. 742-752.
Buysens, K. J. et al., "Generation of 6-alkylidene/benzylidene-3,6-dihyrdopyrazin-2(1H)-ones by reaction of 6-bromomethylpyrazin-2(1H)-ones with methoxide and further conversion into specific piperazine-2,5-diones and pyrazin-2(1H)-ones," Journal of the Chemical Society, Perkin Transactions, Jan. 1, 1996, vol. 3, pp. 231-238, XP009034546.
Buysens, K. J. et al., "Synthesis of New Pyrrolo[3,4-c]pyridine(on)es and Related 1,7-Naphthyridinones and 2,7-Naphthyridines via Intramolecular Diels-Alder Reactions of 2(1H)-Pyrazinones," Tetrahedron, vol. 52, pp. 9161-9178.
Chawla, et al. Curr. Res & Info. Pharm. Sci (Grips), 5, 1, 2004, 9-12.
Jordan, V.C. Nature Reviews: Drug Discovery, 2, 2003, 205.
Dörwald, F. Zaragoza. Side Reactions in Organic Synthesis: A Guide to Successful Synthesis Design, Weinheim: WILEY-VCH Verlag GmbH & Co. KGaA, 2005, Preface.
Hackam, et al. JAMA, 296(14), 2006, 1731-1732.

(Continued)

*Primary Examiner* — Douglas M Willis
(74) *Attorney, Agent, or Firm* — Millen, White, Zelano and Branigan, P.C.

(57) ABSTRACT

Arylpyrazinone derivatives of formula (I),

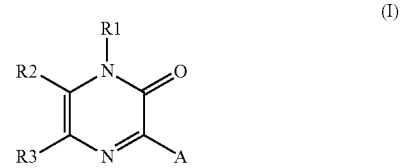

as insulin secretion stimulators, the preparation and use of these pyrazinone derivatives for the prophylaxis and/or treatment of diabetes and pathologies associated.

15 Claims, No Drawings

(56) References Cited

OTHER PUBLICATIONS

Kaval, N. et al. "Transistion metal-catalyzed orthogonal solid-phase decoration of the 2(1H)-Pyrazinone Scaffold Using a Sulfer linker," J. Comb. Chemistry, 2007, vol. 9, pp. 446-453.

Appukkuttan, P. et al., "A chemoselective microwave-assisted one-pot cross-stille reaction of benzylic halides with 2(1H)-Pyrazinones Using Simultaneous Cooling," Sn Lett, 2006, No. 10, pp. 1491-1946.

Rombouts, F. J. R. et al., "Development of a functionalizable external beta-turn mimic base on a cis-fused 1,7-naphthyridine scaffold," Eur. J. Org. Chem., 2-3, pp. 1868-1878.

Loosen, P. K. et al., "Cycloadducts of ethene with 2(1H)-pyrazinones and their conversion into 2,5-diazabicyclo[2.2.2]octane-3,6-diones," Tetrahedron, 1991, vol. 47, No. 44, pp. 9259-9268.

Govaerts, T.C. et al. "Generation of 5,6-dimethylene-2(1H)-pyridinones from [3,4-beta] sulfolene pyridinones and application in Diels-Alder reactions," Tetrahedron, 2004, vol. 60, pp. 429-439.

Kaval, N. et al. "The effect of pressure on microwave-enhanced Diels-alder reactions. A case study," The Royal Society of Chemistry, 2004.

Singh, B.K. et al., "Palladium-catalyzed copper(I)-mediated cross-coupling of arylboronic acids and 2(1H)-pyrazinones facilitated by microwave irradiation with simultaneous cooling," Org. Biomol. Chem., 2007, vol. 5, pp. 2962-2965.

Rombouts, F. J. R. et al., "Intramolecular Diels-Alder reactions of N-alkenyl-2(1H)-pyrazinones : generation of a novel type of cis-1,7-napththyridine," Tetrahedron Letters, 2001, Vo. 42, pp. 739-7399.

Azzam, R. et al., "Expanding the substitution pattern of 2(1H)-pyrazinones via Suzuki and Heck reactions," Tetrahedron, 2005mvol. 61, pp. 3953-3962.

Bhattacharya, B.K. et al., "1[5-Chloro-1-substituted-2(1H)-pyrazin-2-on-3-yl]5-aryl-3-methylpyrazoles," J. Heterocyclic Chem., 1985, vol. 22.

Cheeseman, G. W. H. et al., "Pyrazines. Part IV. 2,6-Dihydroxy-3,5-diphenylpyrazine and Related Compounds," Journal of the Chemical Society, Jan. 1, 1971, vol. 18, pp. 2977-2979.

Habib, M. S. et al., "Mechanism and scope of an N-oxide rearrangement," Journal of the Chemical Society, 1960, pp. 3371-3383.

Habib, M. S. et al., "Rearrangement of certain quinoxalinecarboxanilides. Isolation of an intermediate in a related N-oxide rearrangement," Proceedings of the Chemical Society, 1961, pp. 167-168.

International Search Report for PCT/EP2007/002328 dated Jul. 14, 2009.

Kocevar, M. et al., "Synthesis and transformations of some 1,2,4-oxadiazolylpyrazines," Journal of Heterocyclic Chemistry, 1982, vol. 19, No. 6, pp. 1397-1402, XP002533411.

Nishio, T. et al., "[4+2] Cycloaddition of 2(1H)-Pyrazinones and 1,2,4-Triazoline-3,5-diones," J. Heterocyclic Chem., 1998, vol. 35, pp. 655-658.

Nishio, T. et al., "20. Photochemical Reactions of Tetrahydroquinoxalin-2(1H)-ones and Related Compound," Helvetica Chimica Acta, 1991, vol. 74, pp. 225-231.

Rombouts, F. J. R. et al., "Synthesis and conformational analysis of Substance P antagonist analogues based on a 1,7-naphthyridine scaffold," Tetrahedron, 2003, vol. 59, pp. 4721-4731.

Kocevar, M. et al., "Synthesis and transformations of some 1,2,4-oxadiazolylpyrazines," Journal of Heterocyclic Chemistry, 1982, vol. 19, No. 6, pp. 1397-1402, XP002533411.

METHOD OF STIMULATING INSULIN SECRETION AND/OR MODULATING INS-1 KINASE WITH SUBSTITUTED PYRAZINONES AND/OR SUBSTITUTED TETRAHYDROQUINOXALINONES

FIELD OF THE INVENTION

The present invention relates to arylpyrazinone derivatives of formula (I) as insulin secretion stimulators. The invention also relates to the preparation and use of these pyrazinone derivatives for the prophylaxis and/or treatment of diabetes and pathologies associated.

BACKGROUND OF THE INVENTION

Type 2 diabetes mellitus is one of the most common worldwide diseases. In 2007, its prevalence was estimated at 5.9% (246 million people) of the adult population and is in continuous increase. This disease is even more serious since it could lead to severe micro- and macro-complications, which could become disabling or lethal, as diabetes is a major risk factor for cardiovascular disease and stroke.

Type 2 diabetes is characterized by a fasted and postprandial hyperglycemia, consequence of two main defects: an insulin resistance at the level of target tissues and an altered insulin secretion from the pancreatic beta cells. This latter anomaly seems to appear very early as it is present at the Impaired Glucose Tolerance (IGT) stage (Mitrakou et al., N. Engl. J. Med. 326: 22-29, 1992). It has been observed in UK Prospective Diabetes Study (UKPDS) that 50% of the beta cell function is already lost when diabetes is diagnosed, suggesting that deterioration in beta cell function may begin 10-12 years before diabetes diagnosis (*Holman, Diabetes Res. Clin. Pract.* 40: S21, 1998 *or UKPDS Group, Diabetes* 44: 1249-58, 1995).

The defective insulin secretion is due to a quantitative and a qualitative defect of the beta cell, i.e. a decreased beta cell mass and a specific defect of insulin release in response to glucose, especially the first phase of secretion, since the response to non-glucose secretagogues is preserved (Pfeifer et al., Am. J. Med. 70: 579-88, 1981). The importance of restoring a normal profile of insulin release in response to glucose to maintain the glycemic control within a normal range was supported by studies in non diabetic volunteers showing that delaying the first phase of insulin secretion in response to glucose led to glucose intolerance (Calles-Escandon et al., Diabetes 36: 1167-72, 1987).

Oral antidiabetics available for treatment of type 2 diabetic patients, such as sulfonylureas or glinides, are known to induce insulin secretion, by binding to sulfonylurea receptor on the K-ATP channels of the beta cell, leading to increase in intracellular calcium and insulin exocytosis. This insulin release is thus totally independent of the plasma glucose level and treatment with these molecules usually induces sustained hyperinsulinemia, which could lead to several side-effects, such as severe hypoglycaemia, body weight gain, and aggravation of cardiovascular risk. In addition, the prolonged hyperinsulinemia observed with sulfonylurea treatment, with no preservative effect of the beta cell mass, could lead to secondary failure due to beta cell exhaustion, another deleterious side effect of these compounds.

New treatment of type 2 diabetes should restore a normal profile of insulin release specifically in response to glucose, while preserving or increasing the beta cell mass. This is observed with GLP-1 analogs, such as exenatide or liraglutide, but these molecules are peptides and must be administered by parenteral route.

Such characteristics for a new oral small molecule would be a great advantage over the other antidiabetic drugs.

According to the present invention, the compounds of the formula (I) are insulin secretion stimulators, useful for treatment of diabetes and pathologies associated. They lower blood glucose levels by restoring the defective glucose-induced insulin secretion in type 2 diabetics.

The patent application US 2007082913 describes piperidinylpiperazine compounds for treating chemokine mediated diseases, such as, inflammatory diseases, autoimmune diseases, graft rejection, infectious diseases (e.g. tuberculoid leprosy), fixed drug eruptions, cutaneous delayed-type hypersensitivity responses, type I diabetes, viral meningitis and tumors.

The patent application WO 2004099161 describes pyrazinones as corticotropin releasing factor (CRF1) receptor antagonists for the treatment of CNS and other disorders, particularly anxiety-related disorders and mood disorders.

The patent JP 63301874 describes quinoxalines that exhibit aldose reductase inhibiting activity and are effective to remedy for diabetes complication, such as corneal wound heating defect, cataract, nervous disease, cell membrane disease or renal disease.

SUMMARY OF THE INVENTION

The present invention is directed towards arylpyrazinone derivatives of formula (I). Said derivatives are useful for treating diabetes and pathologies associated therewith. Arylpyrazinone derivatives according to the invention have the following formula (I):

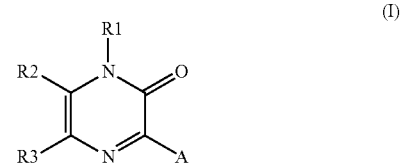

wherein:
R1 is selected from Z;
R2 is selected from hydrogen, alkyl, cycloalkyl;
R3 is selected from hydrogen, halogen, alkyl, cycloalkyl;
A is selected from aryl, heteroaryl, arylalkyl,
wherein alkyl, aryl and heteroaryl groups can be optionally substituted by one or more substituents selected from Y;
Z is:
alkyl, alkenyl, alkynyl, alkoxyalkyl, aryl, arylalkyl, aryloxyalkyl, arylalkoxyalkyl, arylthioalkyl, arylalkylthioalkyl, heteroarylalkyl, heteroaryloxyalkyl, heteroarylalkoxyalkyl, heteroarylthioalkyl, heteroarylalkylthioalkyl, heterocycloalkyl, heterocycloalkylalkyl, heterocycloalkyloxyalkyl, heterocycloalkylalkoxyalkyl, heterocycloalkylthioalkyl, heterocycloalkylalkylthioalkyl, arylalkenyl, arylalkynyl, cycloalkyl, cycloalkylalkyl, cycloalkyloxyalkyl, cycloalkylalkoxyalkyl, cycloalkylthioalkyl, cycloalkylalkylthioalkyl,
each of these groups can be optionally substituted by one or more substituents selected from Y;
Y is:
hydroxy, thio, halogen, cyano, trifluoromethoxy, trifluoromethyl, carboxy, carboxymethyl, carboxyethyl, alkyl, alkoxy, alkylamino, aryl, aryl sulfonylalkyl, aryloxy, arylalkoxy, amino, NR5R6, azido, nitro, guanidino, amidino, phosphono, oxo, carbamoyle, alkylsulfonyl, alkylsulfinyl, alkylthio, $SF_5$, two Y groups can form a methylenedioxy;

R5 and R6 are independently selected from hydrogen, alkyl, aryl, arylalkyl, heteroaryl, heteroarylalkyl, wherein alkyl, aryl and heteroaryl groups can be optionally substituted by one or more substituents selected from Y, R5 and R6 together can constitute an heterocycle;

R2 and R3 can constitute a cycle which corresponds to the general formula (II)

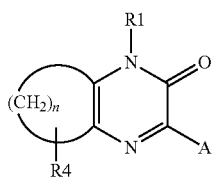

(II)

wherein:

R1 and A are defined as above;

n=3, 4, 5;

R4 represents one or more substituents selected from hydrogen, alkyl, alkoxy, cycloalkyl, aryl, wherein alkyl, cycloalkyl and aryl groups can be optionally substituted by one or more substituents, selected from hydroxy, halogen, alkyl, alkoxy, trifluoromethoxy, trifluoromethyl, alkylsulfonyl, NR7R8;

R7 and R8 are independently selected from hydrogen, alkyl, cycloalkyl;

as well as its racemic forms, tautomers, enantiomers, diastereomers, epimers and polymorphs, and mixtures thereof, and the pharmaceutically acceptable salts thereof;

In another preferred embodiment, the invention provides arylpyrazinone derivatives of formula (I), wherein:

R1 is selected from alkyl, alkenyl, alkynyl, cycloalkyl, cycloalkylalkyl, heterocycloalkyl, heterocycloalkylalkyl, alkoxyalkyl, each of these groups can be optionally substituted by one or more substituents selected from Y;

R2 is selected from hydrogen, alkyl, cycloalkyl;

R3 is selected from hydrogen, halogen, alkyl, cycloalkyl;

A is selected from aryl, heteroaryl, wherein aryl and heteroaryl groups can be optionally substituted by one or more substituents selected from Y;

Y is:

hydroxy, thio, halogen, cyano, trifluoromethoxy, trifluoromethyl, carboxy, carboxymethyl, carboxyethyl, alkyl, alkoxy, alkylamino, aryl, aryl sulfonylalkyl, aryloxy, arylalkoxy, amino, NR5R6, azido, nitro, guanidino, amidino, phosphono, oxo, carbamoyle, alkylsulfonyl, alkylsulfinyl, alkylthio, $SF_5$, two Y groups can form a methylenedioxy;

R5 and R6 are independently selected from hydrogen, alkyl, aryl, arylalkyl, heteroaryl, heteroarylalkyl, wherein alkyl, aryl and heteroaryl groups can be optionally substituted by one or more substituents selected from Y;

R5 and R6 together can constitute an heterocycle;

R2 and R3 can constitute a cycle which corresponds to the general formula (II),

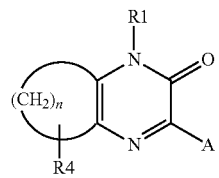

(II)

wherein:

R1 and A are defined as above;

n=3, 4, 5;

R4 represents one or more substituents selected from hydrogen, alkyl, alkoxy, cycloalkyl, aryl;

wherein alkyl, cycloalkyl and aryl groups can be optionally substituted by one or more substituents, selected from hydroxy, halogen, alkyl, alkoxy, trifluoromethoxy, trifluoromethyl, alkylsulfonyl;

as well as its racemic forms, tautomers, enantiomers, diastereomers, epimers and polymorphs, and mixtures thereof, and the pharmaceutically acceptable salts thereof.

In another preferred embodiment, the invention provides pyrazinone derivatives of formula (I), wherein:

R1 is selected from alkyl, cycloalkyl, cycloalkylalkyl, alkoxyalkyl; each of these groups can be optionally substituted by one or more substituents selected from halogen, hydroxy;

preferably, R1 is: ethyl, propyl, isopropyl, butyl; sec-butyl, tert-butyl, cyclopropyl, cyclopropylmethyl;

R2 is selected from hydrogen, alkyl, cycloalkyl;

R3 is hydrogen, alkyl, cycloalkyl, halogen;

preferably R2 and R3 are selected independently from hydrogen, alkyl; more preferably R2 and R3 are hydrogen;

A is selected from aryl, heteroaryl;

wherein aryl and heteroaryl groups can be optionally substituted by one or more substituents selected from Y;

preferably, A is: phenyl, indolyl, quinolinyl; each of these groups can be optionally substituted by one or more groups selected from Y;

Y is:

hydroxy, thio, halogen, cyano, trifluoromethoxy, trifluoromethyl, carboxy, carboxymethyl, carboxyethyl, alkyl, alkoxy, alkylamino, aryl, aryl sulfonylalkyl, aryloxy, arylalkoxy, amino, NR5R6, azido, nitro, guanidino, amidino, phosphono, oxo, carbamoyle, alkylsulfonyl, alkylsulfinyl, alkylthio, $SF_5$, two Y groups can form a methylenedioxy preferably, Y is: halogen, trifluoromethoxy, trifluoromethyl, carboxy, alkyl, alkoxy, alkylsulfonyl, two Y groups can form a methylenedioxy;

R5 and R6 are independently selected from hydrogen, alkyl, aryl, arylalkyl, heteroaryl, heteroarylalkyl;

wherein alkyl, aryl and heteroaryl groups can be optionally substituted by one or more substituents selected from Y;

R5 and R6 together can constitute an heterocycle;

R2 and R3 can constitute a cycle which corresponds to the general formula (II),

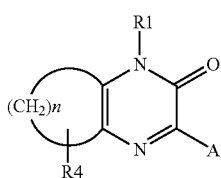
(II)

wherein:
R1 and A are defined as above;
n=3, 4, 5;
R4 represents one or more substituents selected from hydrogen, alkyl, alkoxy, cycloalkyl, aryl;
wherein alkyl, cycloalkyl and aryl groups can be optionally substituted by one or more substituents, selected from hydroxy, halogen, alkyl, alkoxy, trifluoromethoxy, trifluoromethyl, alkylsulfonyl;
preferably, R2 and R3 constitute a cycle, which corresponds to tetrahydroquinoxalin-2(1H)-one;
other preferred compounds are compounds of general formula (I) wherein, when A is a phenyl group, the phenyl group is not substituted in meta position with a phenyl group optionally substituted;
other preferred compounds are compounds of general formula (I) wherein, when R1 is a methyl, A is not 4-substituted-piperidinemethyl;
as well as its racemic forms, tautomers, enantiomers, diastereomers, epimers and polymorphs, and mixtures thereof, and the pharmaceutically acceptable salts thereof.

The compounds of the formula (I) may be chosen from the following compounds:
1-cyclopropyl-3-phenylpyrazin-2(1H)-one;
1-(cyclopropylmethyl)-3-phenylpyrazin-2(1H)-one;
1-ethyl-3-(4-fluorophenyl)pyrazin-2(1H)-one;
1-ethyl-3-(4-methoxyphenyl)pyrazin-2(1H)-one;
1-ethyl-3-(4-methylphenyl)pyrazin-2(1H)-one;
1-ethyl-3-(5-fluoro-2-methoxyphenyl)pyrazin-2(1H)-one;
1-ethyl-3-[4-(methylsulfonyl)phenyl]pyrazin-2(1H)-one;
1-ethyl-3-[4-(trifluoromethoxy)phenyl]pyrazin-2(1H)-one;
1-ethyl-3-[4-(trifluoromethyl)phenyl]pyrazin-2(1H)-one;
1-ethyl-3-phenylpyrazin-2(1H)-one;
1-ethyl-3-(1H-indol-5-yl)pyrazin-2(1H)-one;
1-ethyl-3-(1H-indol-6-yl)pyrazin-2(1H)-one;
1-ethyl-3-quinolin-6-ylpyrazin-2(1H)-one;
1-isopropyl-3-phenylpyrazin-2(1H)-one;
1-butyl-3-phenylpyrazin-2(1H)-one;
1-isobutyl-3-phenylpyrazin-2(1H)-one;
3-(1,3-benzodioxol-5-yl)-1-ethylpyrazin-2(1H)-one;
3-(2-ethoxyphenyl)-1-ethylpyrazin-2(1H)-one;
3-(4-chlorophenyl)-1-(cyclopropylmethyl)pyrazin-2(1H)-one;
3-(4-chlorophenyl)-1-ethyl-5,6,7,8-tetrahydroquinoxalin-2(1H)-one;
3-(4-chlorophenyl)-1-ethylpyrazin-2(1H)-one;
3-(4-chlorophenyl)-1-isobutylpyrazin-2(1H)-one;
3-(4-tert-butylphenyl)-1-ethylpyrazin-2(1H)-one;
3-phenyl-1-propylpyrazin-2(1H)-one;
4-(4-ethyl-3-oxo-3,4-dihydropyrazin-2-yl)benzoic acid;
as well as its racemic forms, tautomers, enantiomers, diastereomers, epimers and polymorphs, and mixtures thereof, and the pharmaceutically acceptable salts thereof.

More preferably, the compounds of the formula (I) according to the invention may be chosen from:
3-(1,3-benzodioxol-5-yl)-1-ethylpyrazin-2(1H)-one;
3-(4-chlorophenyl)-1-(cyclopropylmethyl)pyrazin-2(1H)-one;
3-(4-chlorophenyl)-1-ethyl-5,6,7,8-tetrahydroquinoxalin-2(1H)-one;
3-(4-chlorophenyl)-1-isobutylpyrazin-2(1H)-one;
3-phenyl-1-propylpyrazin-2(1H)-one;
as well as its racemic forms, tautomers, enantiomers, diastereomers, epimers and polymorphs, and mixtures thereof, and the pharmaceutically acceptable salts thereof.

The invention also relates to the racemic forms, tautomeric forms, enantiomers, diastereoisomers, epimers and organic or mineral salts of the compounds of the general formula (I), as well as their crystalline forms, including their polymorphic forms and the polymorphic forms of the compounds of formula (I).

The present invention is directed not only to racemic mixtures of these compounds, but also to individual stereoisomers and/or diastereoisomers thereof, as well or as mixtures of these in all proportions.

The compounds of the invention of the formula (I), as defined above, containing a sufficiently acidic function or a sufficiently basic function, or both, may include the corresponding pharmaceutically acceptable salts of an organic or mineral acid, or of an organic or mineral base.

The expression "pharmaceutically acceptable salts" refers to the relatively non-toxic mineral and organic acid-addition salts, and the base-addition salts, of the compounds of the present invention. These salts may be prepared in situ during the final isolation and purification of the compounds.

In particular, the acid-addition salts may be prepared by separately reacting the purified compound in its purified form with an organic or mineral acid and isolating the salt thus formed. The resulting salts are, for example, hydrochlorides, hydrobromides, sulfates, hydrogenosulfates, dihydrogenophosphates, citrates, maleates, fumarates, trifluoroacetates, 2-naphtalenesulfonates, para-toluenesulfonates.

The invention also relates to pharmaceutically acceptable salts with organic or inorganic bases. In particular, the basic-addition salts may be prepared by separately reacting the purified compound in its purified form with an organic or inorganic base and isolating the salt thus formed. The resulting salts are, for example, metal salts, particularly alkali metal salts, alkaline-earth metal salts and transition metal salts (such as sodium, potassium, calcium, magnesium, aluminum), or salts obtained with bases, such as ammonia or secondary or tertiary amines (such as diethylamine, triethylamine, piperidine, piperazine, morpholine), or with basic amino-acids, or with osamines (such as meglumine), or with aminoalcohols (such as 3-aminobutanol and 2-aminoethanol).

The invention also relates to the salts used for chiral resolution of the racemates.

As examples, the following chiral acids can be used: (+)-D-di-O-benzoyltartaric acid, (−)-L-di-O-benzoyltartaric acid, (−)-L-di-O,O'-p-toluyl-L-tartaric acid, (+)-D-di-O,O'-p-toluyl-L-tartaric acid, (R)-(+)-malic acid, (S)-(−)-malic acid, (+)-camphoric acid, (−)-camphoric acid, R-(−)1,1'-binaphtalen-2,2'-diyl hydrogenophosphonic, (+)-camphanic acid, (−)-camphanic acid, (S)-(+)-2-phenylpropionic acid, (R)-(+)-2-phenylpropionic acid, D-(−)-mandelic acid, L-(+)-mandelic acid, D-tartaric acid, L-tartaric acid, or any mixture of them.

As examples, the following chiral amines can be used: quinine, brucine, (S)-1-(benzyloxymethyl)propylamine (III), (−)-ephedrine, (4S,5R)-(+)-1,2,2,3,4-tetramethyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)-phenylglycinol, (S)-α-methylbenzylamine or any mixture of them.

Also included in the scope of the present invention are prodrugs of the compounds of formula (I).

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s).

In accordance with the present invention and as used herein, the following terms are defined with the following meanings, unless explicitly stated otherwise.

The term "aryl" refers to aromatic groups which have 5-14 ring atoms and at least one ring having a conjugated pi ($\pi$) electron system and includes biaryl groups, all of which may be optionally substituted. Suitable aryl groups include phenyl, naphthyl, biphenyl, anthryl, phenanthryl, indenyl and the like.

The term "heteroaryl" refers to 5-14 ring atom aromatic heterocycles containing 1 to 4 heteroatoms, as ring atoms in the aromatic ring and the remainder of the ring atoms being carbon atoms. Suitable heteroatoms include O, S, N. Suitable heteroaryl groups include furanyl, benzofuranyl, thienyl, pyridyl, pyridyl-N-oxide, pyrimidinyl, pyrazinyl, oxazolyl, thiazolyl, isoxazolyl, quinolinyl, triazolyl, pyridazinyl, pyrrolyl, imidazolyl, indazolyl, isothiazolyl, indolyl, oxadiazolyl and the like.

The term "cycloalkyl" means saturated carbocyclic rings, optionally substituted, and includes mono-, bi- and tri-cyclic compounds with 3 to 10 carbon atoms. Suitable cycloalkyl groups are: cyclopropyl, cyclobutyl, cyclopentyl, cyclohexyl, cycloheptyl, cyclooctyl, cyclodecyl, adamantyl and the like.

The term "heterocycloalkyl" refers to optionally substituted monocyclic, bicyclic or tricyclic radicals, comprising one or more heteroatoms, preferably chosen from among O, S and N, optionally in the oxidized state (for S and N), and optionally one or more double bonds. At least one of the rings preferably comprises from 1 to 4 endocyclic heteroatoms, more preferably from 1 to 3 heteroatoms. Most preferably, the heterocycloalkyl (or simply "heterocyclic" or "heterocycle") radical comprises one or more rings, each having from 5 to 8 nodes. Examples of heterocyclic radicals are: morpholinyl, piperidinyl, piperazinyl, thiazolidinyl, oxazolidinyl, tetrahydrothienyl, dihydrofuranyl, tetrahydrofuranyl, pyrazolidinyl, 1,3-dioxolanyl, pyrrolidinyl, pyranyl, dihydropyranyl, isoxazolidinyl, imidazolyl, imidazolidinyl and the like.

The term "alkyl" refers to a saturated aliphatic groups, including straight chain and branched chain groups. Suitable alkyl groups, having 1 to 20 carbon atoms, include methyl, ethyl, propyl, isopropyl, butyl, sec-butyl, tert-butyl, pentyl, hexyl, octyl, decanoyl, dodecanoyl, hexadecyl, octadecyl groups and the like.

The term "alkenyl" refers to unsaturated groups comprising at least one carbon-carbon double bond, and includes straight chain, branched chain and cyclic groups. Suitable alkenyl groups, having 2 to 20 carbon atoms, include ethenyl, 2-propenyl, 2-butenyl, 3-butenyl, 2-pentenyl, 3-pentenyl, 4-pentenyl and the like.

The term "alkynyl" refers to unsaturated groups comprising at least one carbon-carbon triple bond and includes straight chain, branched chain and cyclic groups; and optionally includes at least one carbon-carbon double bond. Suitable alkynyl groups, having 2 to 20 carbon atoms, include ethynyl, 2-propynyl, 2-butynyl, 3-butynyl, 2-pentynyl, 3-pentynyl, 4-pentynyl and the like.

The term "arylalkyl" refers to an alkyl group, preferably an alkyl group having 1 to 20 carbon atoms, substituted with an aryl group. Suitable arylalkyl groups include benzyl, picolyl, and the like.

The term "arylalkenyl" refers to an alkenyl group, preferably an alkenyl group having 1 to 20 carbon atoms, substituted with an aryl group.

The term "arylalkynyl" refers to an alkynyl group, preferably an alkynyl group having 1 to 20 carbon atoms, substituted with an aryl group.

The term "alkoxy" refers to the group alk-O— wherein "alk" is an alkyl group.

The term "aryloxy" refers to the group aryl-O—.

The term "aryloxyalkyl" refers to an alkyl group substituted with an aryloxy group.

The term "arylalkoxyalkyl" refers to an alkyl group substituted with an arylalkoxy group.

The term "arylalkoxy" refers to the group aryl-Alk-O—, wherein "Alk" is an alkyl group.

The term "arylthioalkyl" refers to an alkyl group substituted with an arylthio group.

The term "alkylsulfinyl" refers to an alkyl-SO— group.

The term "alkylsulfonyl" refers to an alkyl-$SO_2$— group.

The term "aryl sulfonylalkyl" refers to an alkyl group substituted with an arylsulfonyl (aryl-$SO_2$—) group.

The term "arylalkylthioalkyl" refers to an alkyl group substituted with an arylalkylthio.

The term "heteroarylalkyl" refers to an alkyl group substituted with a heteroaryl group.

The term "heteroaryloxyalkyl" refers to an alkyl group substituted with a heteroaryloxy group.

The term "heteroarylalkoxyalkyl" refers to an alkyl group substituted with a heteroarylalkoxy group.

The term "heteroarylthioalkyl" refers to an alkyl group substituted with a heteroarylthio group.

The term "heteroarylalkylthioalkyl" refers to an alkyl group substituted with a heteroarylalkylthio group.

The term "heterocycloalkylalkyl" refers to an alkyl group substituted with a heterocycloalkyl group.

The term "heterocycloalkyloxyalkyl" refers to an alkyl group substituted with a heterocycloalkyloxy group.

The term "heterocycloalkylalkoxyalkyl" refers to an alkyl group substituted with a heterocycloalkylalkoxy group.

The term "heterocycloalkylthioalkyl" refers to an alkyl group substituted with a heterocycloalkylthio group.

The term "heterocycloalkylalkylthioalkyl" refers to an alkyl group substituted with a heterocycloalkylalkylthio group.

The term "cycloalkylalkyl" refers to an alkyl group substituted with a cycloalkyl group.

The term "cycloalkyloxyalkyl" refers to an alkyl group substituted with a cycloalkyloxy group.

The term "cycloalkylalkoxyalkyl" refers to an alkyl group substituted with a cycloalkylalkoxy group.

The terms "alkylthio" refers to the group alkyl-S—.

The term "cycloalkylthio" refers to the group cycloalkyl-S—.

The term "cycloalkylthioalkyl" refers to an alkyl group substituted with a cycloalkylthio group.

The term "cycloalkylalkylthioalkyl" refers to an alkyl group substituted with a cycloalkylalkylthio group.

The term "halogen" refers to a fluorine, bromine or chlorine atom.

The term "amidino" refers to —C(NR5)-NR5R6 where R5R6 are as defined above, all, except hydrogen, are optionally substituted.

The term "carbamoyl" refers to an unsubstituted aminocarbonyl group.

The invention's compounds according to formula (I) exhibit an hypoglycemic activity, and are useful in the treatment of pathologies associated with the syndrome of insulin resistance.

Insulin resistance is characterised by a reduction in the action of insulin (cf. "Presse Medicale", (1997), 26(14), 671-677) and is involved in many pathological conditions, such as diabetes and more particularly non-insulin-dependent diabetes (type II diabetes or NIDDM), dyslipidaemia, obesity, arterial hypertension, and also certain cardiac, microvascular and macrovascular complications, for instance atherosclerosis, retinopathy and neuropathy. In this respect, reference will be made, for Example, to *Diabetes*, 37, (1988), 1595-1607; *Journal of Diabetes and its complications*, 12, (1998), 110-119; *Horm. Res.*, 38, (1992), 28-32.

The invention also relates to pharmaceutical composition containing as active ingredient at least one compound of formula (I), as defined above, and/or a pharmaceutically acceptable salt thereof, in combination with one or several pharmaceutically acceptable carrier, adjuvant, diluent or excipient. A person skilled in the art is aware of a whole variety of such carrier, adjuvant, diluent or excipient compounds suitable to formulate a pharmaceutical composition.

The pharmaceutical compositions of the present invention can be administered by a variety of routes including oral, parenter-al, intravenous, intramuscular, rectal, permucous or percutaneous.

They will thus be presented in the form of injectable solutions or suspensions or multi-dose bottles, in the form of plain or coated tablets, sugar-coated tablets, wafer capsules; gel capsules, pills, sachets, powders, suppositories or rectal capsules, solutions or suspensions, for percutaneous use in a polar solvent, or for permucous use.

The excipients that are suitable for such administrations are pharmaceutically acceptable excipients, such as cellulose or microcrystalline cellulose derivatives, alkaline-earth metal carbonates, magnesium phosphate, starches, modified starches, lactose and the like for solid forms.

For rectal use, cocoa butter or polyethylene glycol stearates are the preferred excipients.

For parenteral use, water, aqueous solutions, physiological saline and isotonic solutions are the vehicles most appropriately used.

For example, in the case of an oral administration, for example in the form of granules, tablets or coated tablets, pills, capsules, gel capsules, gels, cachets or powders, a suitable posology of the compounds is between about 0.1 mg/kg and about 100 mg/kg, preferably between about 0.5 mg/kg and about 50 mg/kg, more preferably between about 1 mg/kg and about 10 mg/kg and most preferably between about 2 mg/kg and about 5 mg/kg of body weight per day.

If representative body weights of 10 kg and 100 kg are considered, in order to illustrate the daily oral dosage range that can be used and as described above, suitable dosages of the compounds of the formula (I) will be between about 1-10 mg/per day and 1000-10000 mg/per day, preferably between about 5-50 mg/per day and 500-5000 mg/per day, more preferably between 10-100 mg and 100-1000 mg/per day and most preferably between 20-200 mg and 50-500 mg/per day.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

As noted above, formulations of the present invention suitable for oral administration may be presented as discrete units, such as capsules, cachets or tablets, each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

In the non-insulin-dependent diabetes, for the man, the hyperglycemia is the results of two main defects: an alteration of the insulin secretion and a reduction in the effectiveness of insulin at level of three sites to knowing the liver, the muscles and adipose tissue.

The present invention also relates to compound of general formula (I) as well as its racemic forms, tautomers, enantiomers, diastereomers, epimers and polymorphs, and mixtures thereof, and the pharmaceutically acceptable salts thereof, for the preparation of a medicament for the prevention and/or treatment of pathologies associated with hyperglycaemia; for the preparation of a medicament that induces insulin secretion in response of glucose concentration, preferably for the treatment of diabetes, more preferably for the prevention and/or treatment of type II diabetes and pathologies associated to metabolic disorders, hypercholesteremia, hyperlipidemia, which are increased by hyperinsulinemia and hyperglycemia; for the treatment of diseases chosen from diabetes related microvascular and macrovascular complications, such as arterial hypertension, inflammatory processes, microangiopathy, macroangiopathy, retinopathy and neuropathy; for reducing hyperglycaemia, for the treatment of dyslipidaemia and obesity; or diseases such as cardiovascular diseases, comprising atherosclerosis, myocardial ischemia.

The present invention also relates to the use of at least a compound of the general formula (I), as well as its racemic forms, tautomers, enantiomers, diastereomers, epimers and polymorphs, and mixtures thereof, and the pharmaceutically acceptable salts, and pro-drugs thereof, for the preparation of a medicament for the prevention and/or treatment of pathologies associated with hyperglycaemia, preferably for the treatment of diabetes, more preferably for the prevention and/or treatment of type II diabetes and pathologies associated to metabolic disorders, hypercholesteremia, hyperlipidemia, which are increased by hyperinsulinemia and hyperglycemia; for the treatment of diseases chosen from diabetes related microvascular and macrovascular complications, such as arterial hypertension, inflammatory processes, microangiopathy, macroangiopathy, retinopathy and neuropathy; for reducing hyperglycaemia, for the treatment of dyslipidaemia and obesity; or diseases such as cardiovascular diseases, comprising atherosclerosis, myocardial ischemia.

The present invention also relates to manufacturing process of compounds of formula (I), as defined above, according to the following representative methods shown in Scheme 1 (Preparation of the intermediates); Scheme 2 (Preparation of arylpyrazinone derivatives, Method A) or Scheme 3 (Preparation of arylpyrazinone derivatives, Method B).

The following schemes are given for representative purposes, and solely for the purpose of facilitating the representation. Needless to say, depending on the nature of the compounds of the formula (I) to be obtained, the methodologies presented may be adapted by a person skilled in the art by selecting the appropriate starting materials, in which the nature of the substituents R1, R2 and R3 may be modified, especially as a function of the nature and length of the desired chain.

The compounds useful according to the invention may be prepared, unless specifically specified, by the application or adaptation of known methods, by which are meant methods used heretofore or described in the literature, patents or patent applications, the Chemical Abstracts and on the Internet.

Preparation of the Intermediates

Scheme 1:

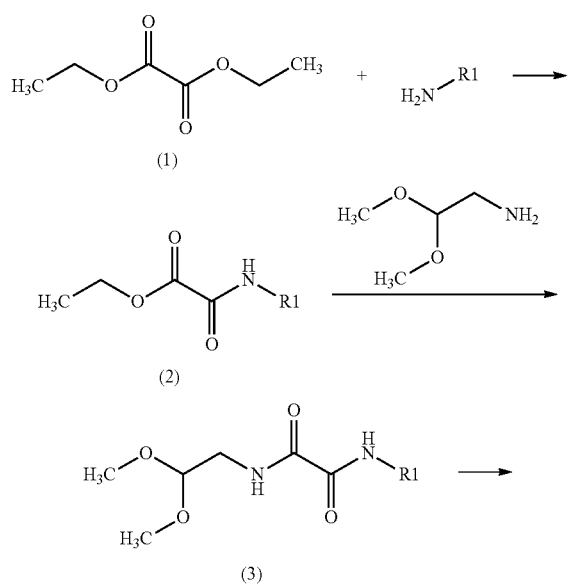

Preparation Of Arylpyrazinone Derivatives.

Scheme 2: Method A

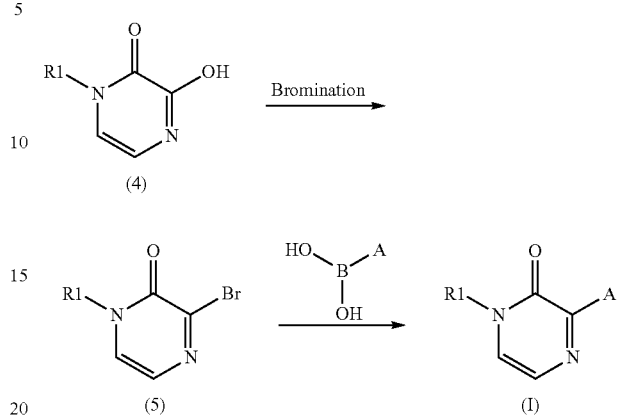

wherein R1 and A are as above defined in formula (I).

3-bromo pyrazinones (5) are prepared by bromination of the corresponding 3-hydroxypyrazinones (4), using a brominating agent, such as $POBr_3$, in an inert solvent, such as 1,2-dichloroethane, at a temperature between 20° C. and the reflux, more preferably reflux, for 1 to 24 h.

Aryl pyrazinones (I) are prepared in reacting the 3-bromopyrazinones (5) with suitable boronic acids or esters (cyclic or not) of boronic acids in the presence of a base, such as sodium carbonate or potassium carbonate, and a catalyst, such as bis(triphenylphosphine) palladium(II)chloride, in an inert solvent, such as dimethylformamide or toluene, at a temperature between 20° C. and the reflux, more preferably reflux, for 1 to 24 h.

Scheme 3: Method B:

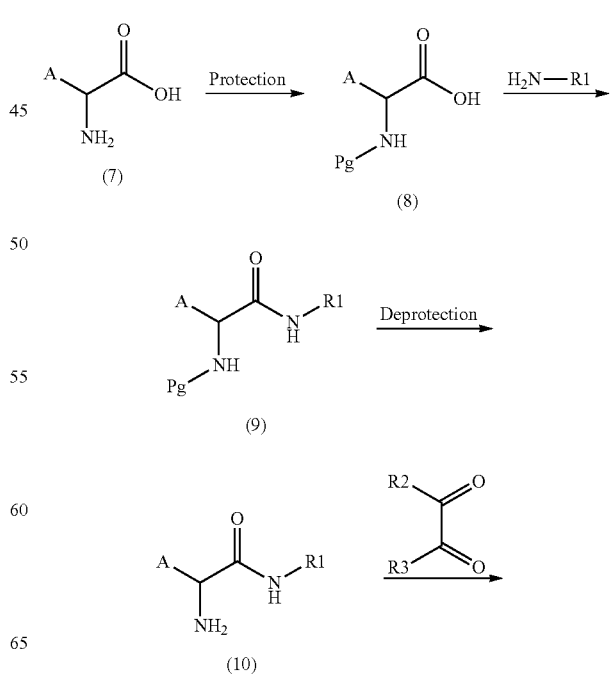

wherein R1 is as above defined in formula (I).

Compounds (2) are prepared by reacting diethyloxalate (1) with an amine in the presence of a quaternary ammonium salt, such as aliquat 336, in an inert solvent, such as chloroform, toluene or dichloromethane, at a temperature between 20° C. and the reflux for 24 to 100 h.

Intermediates (3), with a side chain containing a protected aldehyde in the form of an acetal, are prepared by reacting compounds of formula (2) with a protected aminoacetaldehyde dialkyl-acetate, such as (2,2-dimethoxyethyl)amine. The reaction is carried out in a solvent, such as an alcohol, for example 2-propanol, at a temperature between 20° C. and the reflux, for 1 to 24 h.

Pyrazinones (4) can be prepared by cyclization of compound (3) under acidic conditions, for example in a solvent, such as acetic acid, and catalytic amount of concentrated hydrochloric acid, at a temperature between 20° C. and the reflux for 1 to 24 h.

13

-continued (I)

wherein R1, R2, R3 and A are as above defined in formula (I).

Amino acid derivative is protected using the methods known.

Pg are known protecting groups used for the protection of amines.

Amino function of amino acid derivatives (7) is protected using the methods known in the art. In these formula Pg is a protecting group of the amine function, such as those described by T. W. Greene, Protective groups in Organic Synthesis, J. Wiley-Interscience Publication (1991), preferably a tert-butoxycarbonyl radical or a benzyloxycarbonyl (Cbz) radical.

For example, aminoacid (7) can be protected using di-tert-butyldicarbonate to give compounds (8) in which Pg is a tert-butoxycarbonyl radical.

Amides (9) are prepared in reacting compounds (8) with selected amines. In order to activate the carboxylic acids, coupling agents, such as 1-hydroxybenzotriazole (HOBt) or benzotriazol-1-yl-oxytripyrrolidino phosphonium hexafluoro phosphate (PyBOP) can be used.

Carbonyldiimidazole (CDI) or dicyclohexylcarbodiimide (DCC) can also be used as coupling agents.

Amides (9) can also be prepared directly from corresponding carboxylic acids (8) by in situ generation of mixed anhydride. The coupling reaction is usually carried out in the presence of a tertiary amine, such as N-methylmorpholine (NMM), triethylamine (TEA) or diisopropylethylamine (DIPEA), in an organic solvent chosen from those generally used for amide preparation. Preferred solvents for the coupling reaction are ethylacetate (AcOEt), dimethylformamide (DMF), N-methylpyrrolidone (NMP) or tetrahydrofurane (THF). The mixed anhydride prepared, for example, by treating compounds (8) with isobutyl chloroformate in the presence of 4-methylmorpholine on reaction with amines give compound (9). The reaction can be carried out in a solvent, such as tetrahydrofurane, at a temperature between −50° C. to 0° C., for 1 to 6 h.

Compound (10) is prepared from compound (9) using the methods of deprotection known by those skilled in the art and particularly those described by T. W. Greene, Protective groups in Organic Synthesis, J. Wiley-Interscience Publication (1991). Deprotection of BOC-protected amines can be achieved by using organic acid, such as trifluoroacetic acid ($CF_3COOH$), or mineral acid, such as hydrochloric acid (HCl).

For example amino function of (9) can be deprotected in using hydrochloric acid in dioxane, at a temperature of 0° C. to reflux, preferably at room temperature.

Deprotection reactions can also be carried out by means of catalytic hydrogenation.

Compounds (I) are prepared by reacting compounds (10) with 1,2-dicarbonyl derivatives, such as oxaldehyde, or cyclic 1,2-dione derivatives, such as cyclohexane-1,2-dione or cyclopentane-1,2-dione, optionally substituted. Cyclization can be carried out in a solvent, such as methanol, in the presence of a mineral base, such as sodium hydroxide, at a temperature between −50° C. to 0° C., for 1 to 10 h, preferably between −40° C. and −20° C.

The examples that follow illustrate the invention without, however, limiting it. The starting materials used are known products or products prepared according to known procedures. The percentages are expressed on a weight basis, unless otherwise mentioned.

The compounds were characterised especially via the following analytical techniques.

The NMR spectra were acquired using a Bruker Avance DPX 300 MHz NMR spectrometer.

The masses were determined by HPLC coupled to an Agilent Series 1100 mass detector. The melting points (m.p.) were measured on a Stuart Scientific block.

EXAMPLES

Example 1

Ethyl(ethylamino)(oxo)acetate

To 135,8 ml (1000 mM) of diethyloxalate and 1 g of aliquat 336, in 1000 ml of dichloromethane, were added 64 ml (1000 mM) of ethylamine at 70% in water. The reaction mixture was stirred at room temperature for 72 h. The reaction mixture was dried over anhydrous sodium sulfate and the solvent was removed under vacuum to give an oil, which was further purified by silica gel column chromatography, using dichloromethane/dimethylketone (95/5) as eluant, to give 59.9 g of ethyl(ethyl amino)(oxo)acetate as an oil.

Yield: 41.3%.

NMR $^1H$ (300 MHz/DMSO-d6) δ (ppm): 1.06(t, 3H), 1.28 (t, 3H), 3.17(m, 2H), 4.22(q, 2H), 8.92(s, 1H)

Example 2

N-(2,2-dimethoxyethyl)-N'-ethylethanediamide

-continued

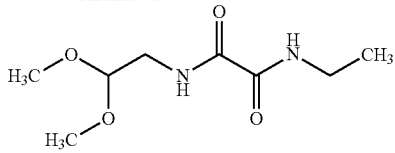

59.9 g (412.6 mM) of ethyl(ethylamino)(oxo)acetate and 45 ml (412.6 mM) of (2,2-dimethoxyethyl)amine, in 480 ml of 2-propanol, were stirred at room temperature for 16 h. A white precipitate was filtered, washed with 2-propanol and dried under vacuum to give 67.8 g of N-(2,2-dimethoxyethyl)-N'-ethylethanediamide.

Yield: 80.5%.

NMR $^1$H (300 MHz/DMSO-d6) δ (ppm): 1.07(t, 3H), 3.15 (m, 2H), 3.27(m, 8H), 4.51(m, 1H), 8.62(m, 1H), 8.81(m, 1H)

Example 3

1-ethyl-3-hydroxypyrazine-2(1H)-one

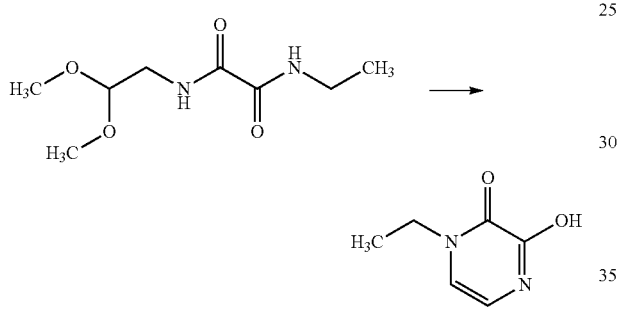

67.5 g (330 mM) of N-(2,2-dimethoxyethyl)-N'-ethylethanediamide and 2 ml of concentrated hydrochloric acid, in 390 ml of acetic acid, were refluxed under stirring for 1 h. The solvent was removed under vacuum to give an oil, which was further purified by silica gel column chromatography, using dichloromethane/methanol (95/5) as eluant to give 37 g of 1-ethyl-3-hydroxy pyrazine-2(1H)-one as an oil.

Yield: 79.5%.

NMR $^1$H (300 MHz/DMSO-d6) δ (ppm): 1.20(t, 3H), 3.73 (q, 2H), 6.34(d, 1H), 6.56(d, 1H), 11.22(s, 1H)

Method A

Example 4

3-bromo-1-ethylpyrazin-2(1H)-one

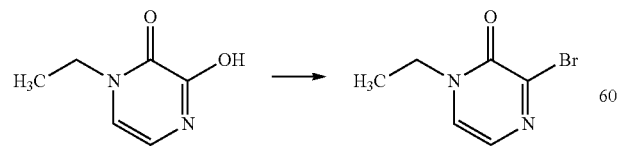

10.5 g (75 mM) of 1-ethyl-3-hydroxypyrazine-2(1H)-one and 23.1 g (80.5 mM) of phosphorous oxybromide in 75 ml of dichloroethane were refluxed under stirring for 2 h. The reaction mixture was then neutralized to pH 7-8 with a saturated aqueous solution of sodium carbonate, while maintaining the temperature at 10° C. The reaction mixture was then stirred at room temperature for 1 h. Water was added and the organic phase was extracted with dichloromethane. The combined organic layer was washed with water, dried on anhydrous sodium sulfate and the solvent was removed under vacuum. The compound was further purified by silica gel column chromatography using dichloromethane as eluant to give 6.1 g of 3-bromo-1-ethylpyrazin-2(1H)-one as a solid.

Yield: 40.2%.

NMR $^1$H (300 MHz/DMSO-d6) δ (ppm): 1.18(t, 3H), 3.87 (q, 2H), 7.13(d, 1H), 7.75(d, 1H)

The following compounds were obtained using the same procedure as in Example 4:

Example 4-2

3-bromo-1-methylpyrazin-2(1H)-one

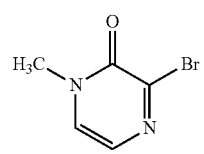

NMR $^1$H (300 MHz/DMSO-d6) δ (ppm): 3.51(s, 3H), 7.18 (d, 1H), 7.80(d, 1H)

Example 4-3

3-bromo-1-butylpyrazin-2(1H)-one

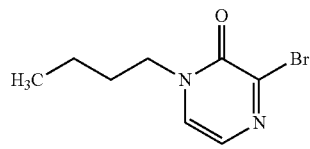

NMR $^1$H (300 MHz/DMSO-d6) δ (ppm): 0.90(t, 3H), 1.30 (m, 2H), 1.65(m, 2H), 3.93(t, 2H), 7.20(d, 1H), 7.79(d, 1H)

Example 4-4

3-bromo-1-propylpyrazin-2(1H)-one

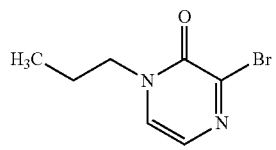

$C_7H_9BrN_2O$=217.06 Mass 218.0 (M+1)

Example 5

3-(4-chlorophenyl)-1-ethylpyrazin-2(1H)-one

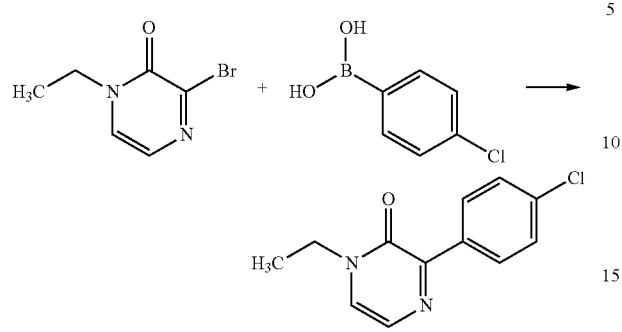

To 200 mg (0.98 mM) of 3-bromo-1-ethylpyrazin-2(1H)-one and 57 mg (0.05 mM) of palladium tetrakis triphenylphosphine in 4 ml of toluene were added, under nitrogen, 231.0 mg (1.48 mM) of 4-chlorophenylboronic acid and 2.9 ml of 2M sodium carbonate aqueous solution. The mixture was stirred for 3 h at reflux under nitrogen atmosphere, and then at room temperature overnight. Water was added and the mixture was extracted with ethyl acetate. The organic phase was separated, dried, over anhydrous sodium sulfate, and concentrated. The compound was purified through a silica plug, eluting with dichloromethane, which afforded 110 mg of 3-(4-chlorophenyl)-1-ethylpyrazin-2(1H)-one as a solid.
Yield: 56%.
NMR $^1$H (300 MHz/DMSO-d6) δ (ppm): 1.31(t, 3H), 4.03 (q, 2H), 7.50(m, 3H), 7.81(d, 1H), 8.30(m, 2H)
$C_{12}H_{11}ClN_2O$=234.68 Mass 235.0 (M+1)

Example 5-2

1-ethyl-3-[4-(methylsulfonyl)phenyl]pyrazin-2(1H)-one

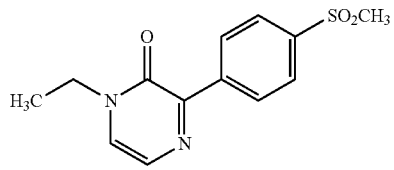 [SMILES: CCn1ccnc(-c2ccc(S(C)(=O)=O)cc2)c1=O]

NMR $^1$H (300 MHz/DMSO-d6) δ (ppm): 1.31(t, 3H), 3.01 (s, 3H), 4.03(q, 2H), 6.52(d, 1H), 7.94(d, 2H), 8.06(d, 2H), 8.38(d, 1H)
m.p.: 108-110° C.

Example 5-3

1-ethyl-3-(1H-indol-5-yl)pyrazin-2(1H)-one

$C_{14}H_{13}N_3O$=239.27 Mass 240.1 (M+1)

Example 5-4

3-(2-ethoxyphenyl)-1-ethylpyrazin-2(1H)-one

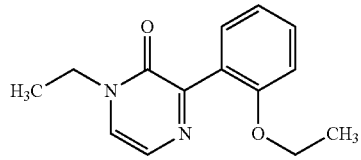 [SMILES: CCOc1ccccc1-c1nccn(CC)c1=O]

$C_{14}H_{16}N_2O_2$=244.29 Mass 245.1 (M+1)

Example 5-5

3-(1,3-benzodioxol-5-yl)-1-ethylpyrazin-2(1H)-one

$C_{13}H_{12}N_2O_3$=244.25 Mass 245.1 (M+1)

Example 5-6

1-ethyl-3-[4-(trifluoromethoxy)phenyl]pyrazin-2(1H)-one

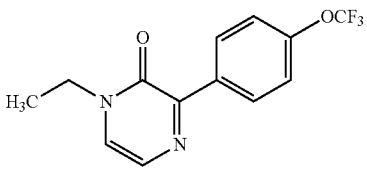 [SMILES: CCn1ccnc(-c2ccc(OC(F)(F)F)cc2)c1=O]

$C_{13}H_{11}F_3N_2O_2$=284.23 Mass 285.1 (M+1)

Example 5-7

1-ethyl-3-(5-fluoro-2-methoxyphenyl)pyrazin-2(1H)-one

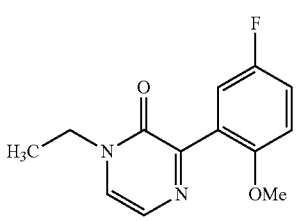 [SMILES: CCn1ccnc(-c2cc(F)ccc2OC)c1=O]

$C_{13}H_{13}FN_2O_2$=248.25 Mass 249.1 (M+1)

Example 5-8

3-(4-tert-butylphenyl)-1-ethylpyrazin-2(1H)-one

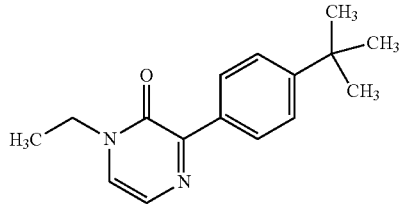 [SMILES: CCn1ccnc(-c2ccc(C(C)(C)C)cc2)c1=O]

$C_{16}H_{20}N_2O=256.34$ Mass 257.1 (M+1)

Example 5-9

1-ethyl-3-(4-methoxyphenyl)pyrazin-2(1H)-one

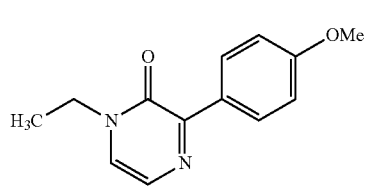 [SMILES: CCn1ccnc(-c2ccc(OC)cc2)c1=O]

$C_{13}H_{14}N_2O_2=230.26$ Mass 231.1 (M+1)

Example 5-10

1-ethyl-3-[4-(trifluoromethyl)phenyl]pyrazin-2(1H)-one

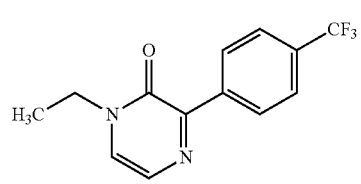 [SMILES: CCn1ccnc(-c2ccc(C(F)(F)F)cc2)c1=O]

$C_{13}H_{11}F_3N_2O=268.23$ Mass 269.0 (M+1)

Example 5-11

1-ethyl-3-(4-fluorophenyl)pyrazin-2(1H)-one

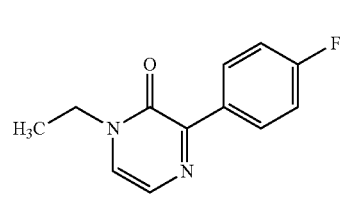 [SMILES: CCn1ccnc(-c2ccc(F)cc2)c1=O]

$C_{12}H_{11}FN_2O=218.23$ Mass 219.0 (M 1)

Example 5-12

1-ethyl-3-(4-methy phenyl)pyrazin-2(1H)-one

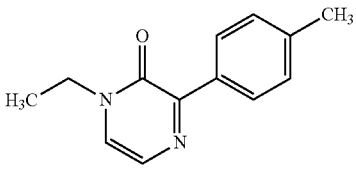 [SMILES: CCn1ccnc(-c2ccc(C)cc2)c1=O]

$C_{13}H_{14}N_2O=214.26$ Mass 215.1 (M+1)

Example 5-13

1-ethyl-3-phenylpyrazin-2(1H)-one

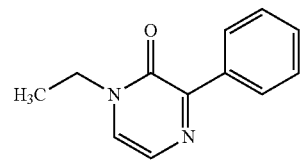

$C_{12}H_{12}N_2O=200.24$ Mass 201.1 (M+1)

Example 5-14

1-ethyl-3-quinolin-6-ylpyrazin-2(1H)-one

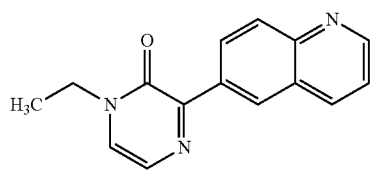 [SMILES: CCn1ccnc(-c2ccc3ncccc3c2)c1=O]

$C_{15}H_{13}N_3O=251.28$ Mass 252.1 (M+1)

Example 5-15

4-(4-ethyl-3-oxo-3,4-dihydropyrazin-2-yl)benzoic acid

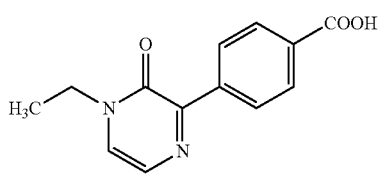 [SMILES: CCn1ccnc(-c2ccc(C(=O)O)cc2)c1=O]

NMR $^1$H (300 MHz/CDCl$_3$) δ (ppm): 1.38(t, 3H), 3.99(q, 2H), 7.18(d, 1H), 7.47(d, 1H), 8.10(m, 2H), 8.39(m, 2H)
m.p.: 170° C.

Example 5-16

1-ethyl-3-(1H-indol-6-yl)pyrazin-2(1H)-one

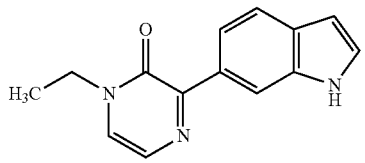 [SMILES: CCn1ccnc(-c2ccc3cc[nH]c3c2)c1=O]

C$_{14}$H$_{13}$N$_3$O=239.27 Mass 240.1 (M+1)
m.p.: 170° C.

Example 6

[(tert-butoxycarbonyl)amino](4-chlorophenyl)acetic acid

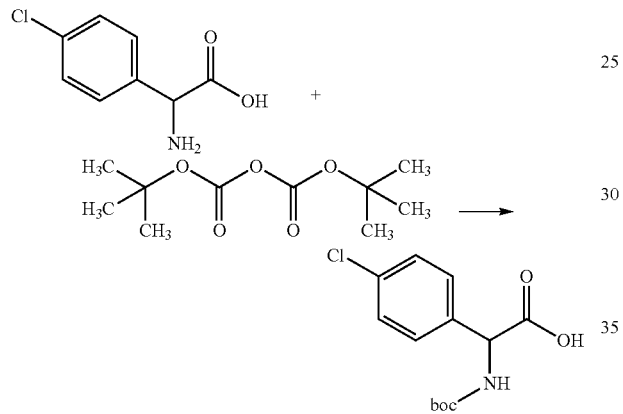

To 25 g (134.6 mM) of amino(4-chlorophenyl)acetic in 270 ml of a 1N aqueous solution of sodium hydroxide were added 34 g (156 mM) of di-tert-butyldicarbonate. The mixture was stirred at room temperature for 16 h. The reaction mixture was extracted twice with ethyl acetate. The combined organic layer was washed with water and dried over anhydrous sodium sulfate. The solvent was removed under vacuum to give 34.3 g of [(tert-butoxycarbonyl)amino](4-chlorophenyl)acetic acid as a yellow oily compound.

Yield: 89.2%.

NMR $^1$H (300 MHz/DMSO-d6) δ (ppm): 1.40(s, 9H), 5.14 (d, 1H), 7.42(m, 4H), 7.62(d, 1H)

Example 7 tert-butyl 1-(4-chlorophenyl)-2-(ethylamino)-2-oxo-ethylcarbamate

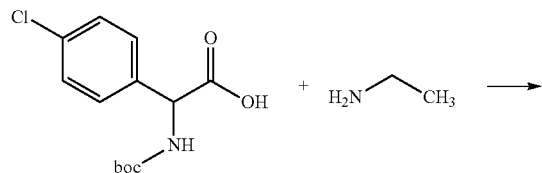

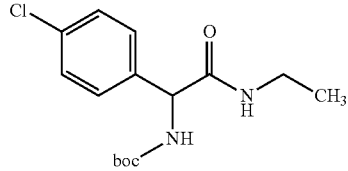

To 1.1 g (3.85 mM) of [(tert-butoxycarbonyl)amino](4-chlorophenyl)acetic acid in 10 ml of tetrahydrofurane were added, under stirring at −25° C., 0.5 ml (4.6 mM) of 4-methyl morpholine and 0.52 ml (4.0 mM) of isobutyl chloroformate. After 10 mn were then added, at −25° C. under stirring, 1.9 ml (3.85 mM) of ethylamine 2M in tetrahydrofurane. The reaction mixture was stirred at −25° C. for 1 h, and at room temperature for 16 h. The reaction mixture was filtered and the filtrate was concentrated under vacuum to give an oil, which was further purified by silica gel column chromatography, using dichloromethane/cyclohexane (75/25) as eluant, to give 520 mg of tert-butyl 1-(4-chlorophenyl)-2-(ethylamino)-2-oxoethylcarbamate as a white solid.

Yield: 43%.

NMR $^1$H (300 MHz/DMSO-d6) δ (ppm): 0.99(t, 3H), 1.39 (s, 9H), 3.08(m, 2H), 5.14(d, 1H), 7.35(d, 1H), 7.42(s, 4H), 8.19(t, 1H)

Example 8

2-amino-2-(4-chlorophenyl)-N-ethylacetamide

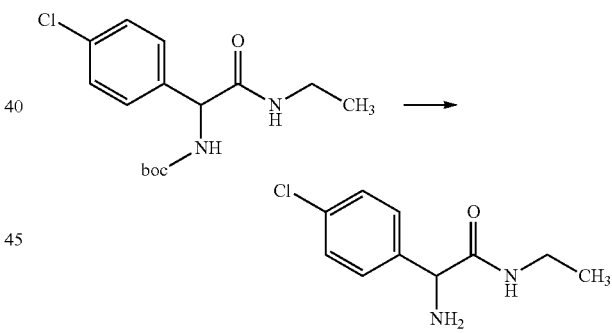

A solution of 516 mg (1.65 mM) of tert-butyl 1-(4-chlorophenyl)-2-(ethylamino)-2-oxoethylcarbamate in 2 ml of 4N hydrochloric acid-dioxane solution were stirred at room temperature for 2 h. The reaction mixture was neutralized with an aqueous solution of sodium hydrogenocarbonate and was extracted twice with ethyle acetate. The combined organic layer was washed with water and dried over anhydrous sodium sulfate. The solvent was removed under vacuum to give 350 mg of 2-amino-2-(4-chlorophenyl)-N-ethylacetamide as an oil.

Yield: 99.8%.

NMR $^1$H (300 MHz/DMSO-d6) δ (ppm): 1.01(t, 3H), 2.27, (s, 2H), 3.08(m, 2H), 4.32(s, 1H), 4.32(s, 1H), 7.39(m, 4H), 8.09(m, 1H)

The following compounds were obtained using the same procedure as in Example 8

Example 8-2

2-amino-N-cyclopropyl-2-phenylacetamide, hydrochloride

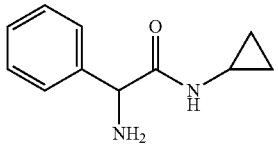 [SMILES: NC(C(=O)NC1CC1)c1ccccc1]

NMR ¹H (300 MHz/DMSO-d6) δ (ppm): 0.24(m, 4H), 2.46(m, 1H), 4.72(s, 1H), 7.22(m, 3H), 7.39(m, 2H), 8.62(s, 3H), 8.85(d, 1H)

Example 8-3

2-amino-N-(cyclopropylmethyl)-2-phenylacetamide, hydrochloride

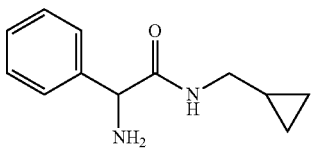 [SMILES: NC(C(=O)NCC1CC1)c1ccccc1]

NMR ¹H (300 MHz/DMSO-d6) δ (ppm): 0.10(m, 2H), 0.35(m, 2H), 0.83(m, 1H), 2.95(m, 2H), 4.99(s, 1H), 7.39(m, 3H), 7.49(m, 2H), 8.72(m, 4H)

Example 8-4

2-amino-N-(tert-butyl)-2-(4-chlorophenyl)acetamide, hydrochloride

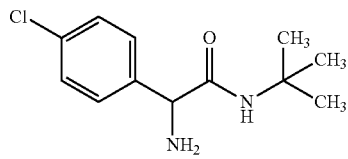 [SMILES: CC(C)(C)NC(=O)C(N)c1ccc(Cl)cc1]

NMR ¹H (300 MHz/DMSO-d6) δ (ppm): 1.24(s, 9H), 4.97 (s, 1H), 7.56(s, 4H), 8.40(s, 1H), 8.72(s, 3H)

Example 8-5

2-amino-2-(4-chlorophenyl)-N-isobutylacetamide, hydrochloride

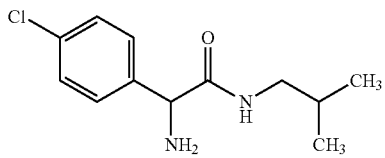 [SMILES: CC(C)CNC(=O)C(N)c1ccc(Cl)cc1]

NMR ¹H (300 MHz/DMSO-d6) δ (ppm): 0.75(dd, 6H), 1.68(m, 1H), 2.94(m, 2H), 3.59(s, 1H), 7.57(s, 4H), 8.60(m, 1H), 8.70(s, 3H)

Example 8-6

2-amino-N-isopropyl-2-phenylacetamide, hydrochloride

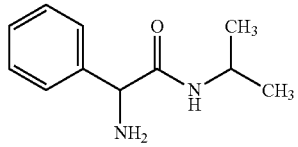

NMR ¹H (300 MHz/DMSO-d6) δ (ppm): 0.96(d, 3H), 1.13(d, 3H), 3.85(m, 1H), 4.95(m, 1H), 7.42(m, 3H), 7.57(m, 2H), 8.82(m, 4H)

Example 9

3-(4-chlorophenyl)-1-ethyl-5,6,7,8-tetrahydroquinoxalin-2(1H)-one

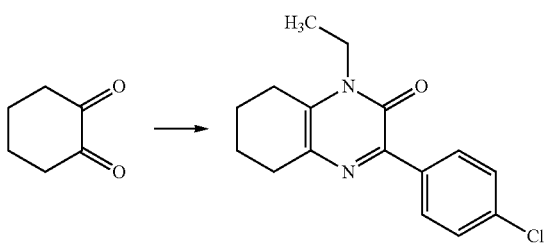

To 330 mg (1.55 mM) of 2-amino-2-(4-chlorophenyl)-N-ethylacetamide in 3.5 ml of methanol at −35° C. were added 174.1 mg (1.55 mM) of cyclohexane-1,2-dione and 310 µl of a 10N aqueous solution of sodium hydroxide. After stirring at −35° C. for one hour, the reaction mixture was then stirred at 5° C. for 3 h and at room temperature for 16 h. After addition of water, the reaction mixture was acidified with hydrochloric acid and extracted twice with dichloromethane. The combined organic layer was separated, washed with water, dried over anhydrous sodium sulfate, and the solvent was then removed under vacuum to give a brown solid, which was further purified by silica gel column chromatography, using dichloromethane/cyclohexane (75/25) as eluant, to give 192 mg of 3-(4-chlorophenyl)-1-ethyl-5,6,7,8-tetrahydroquinoxalin-2(1H)-one as a yellow solid. Yield: 42.8%.

NMR ¹H (300 MHz/DMSO-d6) δ (ppm): 1.24(t, 3H), 1.78 (m, 4H), 2.70(t, 2H), 2.83(t, 2H), 4.08(q, 2H), 7.48(d, 2H), 8.37(d, 2H)

$C_{16}H_{17}ClN_2O=288.77$ Mass 289.1 (M+1)

m.p.: 110-113° C.

The following compounds were obtained using the same procedure as in Example 9:

Example 9-2

1-cyclopropyl-3-phenylpyrazin-2(1H)-one

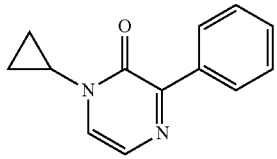 [SMILES: O=c1c(-c2ccccc2)nccn1C1CC1]

$C_{13}H_{12}N_2O$=212.25 Mass 213.1 (M+1)

Example 9-3

3-phenyl-1-propylpyrazin-2(1H)-one

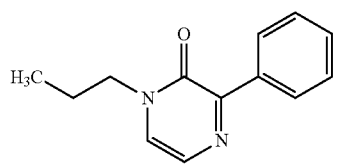 [SMILES: CCCn1ccnc(-c2ccccc2)c1=O]

$C_{13}H_{14}N_2O$=214.26 Mass 215.1 (M 1)

Example 9-4

1-butyl-3-phenylpyrazin-2(1H)-one

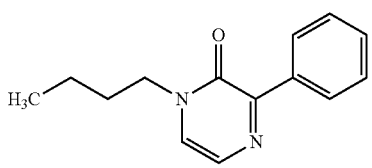 [SMILES: CCCCn1ccnc(-c2ccccc2)c1=O]

NMR $^1$H (300 MHz/DMSO-d6) δ (ppm): 0.86(t, 3H), 1.42 (m, 2H), 1.82(m, 2H), 4.97(m, 2H), 7.49(m, 3H), 7.60(d, 1H), 7.79(d, 1H), 8.31(m, 2H)

Example 9-5

1-isobutyl-3-phenylpyrazin-2(1H)-one

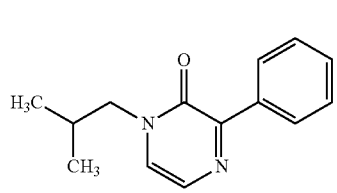 [SMILES: CC(C)Cn1ccnc(-c2ccccc2)c1=O]

$C_{14}H_{16}N_2O$=228.29 Mass 229.1 (M+1)

Example 9-6

1-(cyclopropylmethyl)-3-phenylpyrazin-2(1H)-one

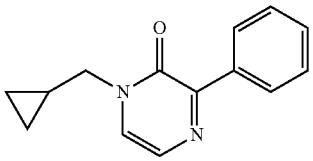 [SMILES: O=c1c(-c2ccccc2)nccn1CC1CC1]

NMR $^1$H (300 MHz/DMSO-d6) δ (ppm): 0.21(m, 2H), 0.30(m, 2H), 1.,04(m, 1H), 3.62(d, 2H), 7.21(m, 3H), 7.28(d, 1H), 7.58(d, 1H), 8.05(m, 2H)

Example 9-7

3-(4-chlorophenyl)-1-isobutylpyrazin-2(1H)-one

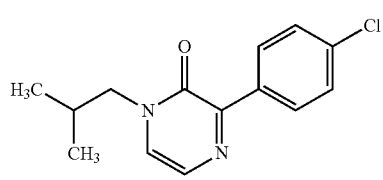 [SMILES: CC(C)Cn1ccnc(-c2ccc(Cl)cc2)c1=O]

$C_{14}H_{15}Cl N_2O$=262.73 Mass 263.1 (M+1)

Example 9-8

3-(4-chlorophenyl)-1-(cyclopropylmethyl)pyrazin-2(1H)-one

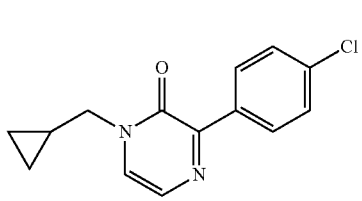 [SMILES: O=c1c(-c2ccc(Cl)cc2)nccn1CC1CC1]

$C_{14}H_{13}Cl N_2O$=260.72 Mass 261.1 (M+1)

Example 9-9

1-isopropyl-3-phenylpyrazin-2(1H)-one

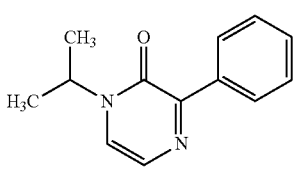 [SMILES: CC(C)n1ccnc(-c2ccccc2)c1=O]

NMR $^1$H (300 MHz/DMSO-d6) δ (ppm): 1.43(d, 6H), 5.15(m, 1H), 7.49(m, 3H), 7.59(d, 1H), 7.84(d, 1H), 8.30(m, 2H)

Biological Assays

The INS-1 cells were selected to evaluate our compounds for their superior response to glucose and other physiological and pharmacological insulin secretagogues.

Culture of Pancreatic INS-1 Cells

INS-1 cells were cultured in complete medium, RPMI1640 containing 1 mM sodium pyruvate, 50 µM 2-mercaptoethanol, 2 mM glutamine, 10 mM HEPES, 100 IU/mL penicillin, and 100 µg/mL streptomycin (CM), supplemented with 10 mM glucose, and 10% (vol/vol) heat-inactivated fetal calf serum (FCS), as described by Asfari et al. (Endocrinology 130: 167-178, 1992).

Insulin Secretion Assay

INS-1 cells were plated and cultured in 48-well plates. After 2 days of culture, the medium was removed and cells were cultured for 24 h with a medium change to 5 mM glucose, 1% FCS. The cells were then washed with Krebs-Ringer Bicarbonate HEPES buffer (KRBH; 135 mM NaCl; 3.6 mM KCl; 5 mM NaHCO3; 0.5 mM NaH2PO4; 0.5 mM MgCl2; 1.5 mM CaCl2 and 10 mM HEPES; pH 7.4) 0.1% BSA containing 2.8 mM glucose and preincubated for 30 min at 37° C. in the same buffer. The cells were then washed twice and incubated for 1 h in KRBH 0.1% BSA containing 4.2 mM glucose and different concentrations of the tested molecule. Insulin concentration in the collected supernatants was measured with ELISA using rat insulin antibody (Insulin Rat Elit PLUS, cat. ref 10-1145-01).

Insulin secretion results are expressed in % of control (glucose 4.2 mM).

Insulin Secretion in INS-1 Cells (Glucose at 4.2 mM)

| Example | % of ctrl at 10 µM of cpd | % of ctrl at 50 µM of cpd |
|---|---|---|
| 9 | 343 | 371 |
| 9-3 | 145 | 182 |
| 9-7 | 140 | 338 |
| 9-8 | 172 | 333 |
| 5-5 | 158 | 204 |

The invention claimed is:

1. A method of stimulating insulin secretion in a host and/or a method of modulating INS-1 kinase activity in a host, comprising administering to a host in need thereof an effective amount of a compound of formula (I)

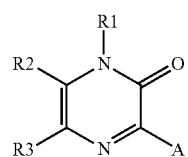

wherein:
R1 is Z;
R2 is hydrogen, alkyl, or cycloalkyl;
R3 is hydrogen, halogen, alkyl, or cycloalkyl;
A is aryl, heteroaryl, or arylalkyl,
A is selected aryl, heteroaryl, or arylalkyl,
wherein alkyl, aryl and heteroaryl groups can be optionally substituted by one or more substituents Y;
Z is:
alkyl, alkenyl, alkynyl, alkoxyalkyl, aryl, arylalkyl, aryloxyalkyl, arylalkoxyalkyl, arylthioalkyl, arylalkylthioalkyl, heteroarylalkyl, heteroaryloxyalkyl, heteroarylalkoxyalkyl, heteroarylthioalkyl, heteroarylalkylthioalkyl, heterocycloalkyl, heterocycloalkylalkyl, heterocycloalkyloxyalkyl, heterocycloalkylalkoxyalkyl, heterocycloalkylthioalkyl, heterocycloalkylalkylthioalkyl, arylalkenyl, arylalkynyl, cycloalkyl, cycloalkylalkyl, cycloalkyloxyalkyl, cycloalkylalkoxyalkyl, cycloalkylthioalkyl, or cycloalkylalkylthioalkyl, each of these groups can be optionally substituted by one or more substituents Y;
Y is:
hydroxy, thio, halogen, cyano, trifluoromethoxy, trifluoromethyl, carboxy, carboxymethyl, carboxyethyl, alkyl, alkoxy, alkylamino, aryl, aryl sulfonylalkyl, aryloxy, arylalkoxy, NR5R6, azido, nitro, guanidino, amidino, phosphono, oxo, carbamoyle, alkylsulfonyl, alkylsulfinyl, alkylthio, or SF$_5$ and two Y groups can optionally form a methylenedioxy;
R5 and R6 are independently hydrogen, alkyl, aryl, arylalkyl, heteroaryl, or heteroarylalkyl,
wherein alkyl, aryl and heteroaryl groups can be independently optionally substituted by one or more substituents Y, or
R5 and R6 together can optionally constitute a heterocycle;
or R2 and R3 can constitute a cycle compound then corresponds to formula (II)

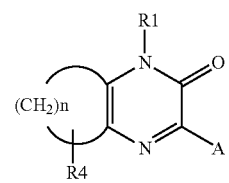

wherein:
n is 4;
R4 is one or more hydrogen, alkyl, alkoxy, cycloalkyl, or aryl,
wherein alkyl, cycloalkyl and aryl groups can be optionally substituted by one or more hydroxy, halogen, alkyl, alkoxy, trifluoromethoxy, trifluoromethyl, alkylsulfonyl, or NR7R8; and
R7 and R8 are independently hydrogen, alkyl, or cycloalkyl;
or racemic forms, tautomers, enantiomers, diastereomers, epimers, or mixtures thereof, or pharmaceutically acceptable salts thereof.

2. The method according to claim 1, wherein in the compound of formula (I):
R1 is alkyl, cycloalkyl, cycloalkylalkyl, or alkoxyalkyl;
wherein each of these groups can be, independently optionally substituted by one or more halogen, or hydroxy;
R2 is hydrogen, alkyl, or cycloalkyl;
R3 is hydrogen, alkyl, cycloalkyl, or halogen;
A is aryl, or heteroaryl;
wherein aryl and heteroaryl groups can be independently optionally substituted by one or more substituents Y;
Y is:
hydroxy, thio, halogen, cyano, trifluoromethoxy, trifluoromethyl, carboxy, carboxymethyl, carboxyethyl, alkyl, alkoxy, alkylamino, aryl, aryl sulfonylalkyl, aryloxy, arylalkoxy, NR5R6, azido, nitro, guanidino, amidino, phosphono, oxo, carbamoyl, alkylsulfonyl, alkylsulfinyl, alkylthio, or $SF_5$, and two Y groups can optionally form methylenedioxy, R5 and R6 are independently hydrogen, alkyl, aryl, arylalkyl, heteroaryl, or heteroarylalkyl;

wherein alkyl, aryl and heteroaryl groups can be independently optionally substituted by one or more substituents Y; or R5 and R6 together can optionally constitute a heterocycle; or R2 and R3 can constitute a cycle which compound then corresponds to formula (II),

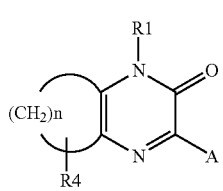

(II)

wherein:
n is 4; and
R4 is one or more hydrogen, alkyl, alkoxy, cycloalkyl, or aryl;
wherein alkyl, cycloalkyl and aryl groups can be optionally substituted by one or more hydroxy, halogen, alkyl, alkoxy, trifluoromethoxy, trifluoromethyl, or alkylsulfonyl;
or racemic forms, tautomers, enantiomers, diastereomers, epimers, or mixtures thereof, or pharmaceutically acceptable salts thereof.

3. The method according to claim 2, wherein R1 is ethyl, propyl, isopropyl, butyl, cyclopropyl, or cyclopropylmethyl.

4. The method according to claim 2, wherein R2 and R3 are independently hydrogen, alkyl or constitute a cycle, which corresponds to tetrahydroquinoxalin-2(1H)-one.

5. The method according to claim 2, wherein R2 and R3 are hydrogen, or constitute a cycle, which corresponds to tetrahydroquinoxalin-2(1H)-one.

6. The method according to claim 2, wherein A is phenyl, indolyl, or quinolinyl, wherein each of these groups can be optionally substituted by one or more groups Y.

7. The method according to claim 2, wherein Y is halogen, trifluoromethoxy, trifluoromethyl, carboxy, alkyl, alkoxy, alkylsulfonyl, and two Y groups can optionally form a methylenedioxy.

8. The method according to claim 1, wherein in the compound of formula (I):
R1 is alkyl, alkenyl, alkynyl, cycloalkyl, cycloalkylalkyl, heterocycloalkyl, heterocycloalkylalkyl, or alkoxyalkyl,
wherein each of these groups can be independently optionally substituted by one or more substituents Y;
R2 is hydrogen, alkyl, or cycloalkyl;
R3 is hydrogen, halogen, alkyl, or cycloalkyl;
A is aryl, or heteroaryl,
wherein aryl and heteroaryl groups can be optionally substituted by one or more substituents Y;
Y is:
hydroxy, thio, halogen, cyano, trifluoromethoxy, trifluoromethyl, carboxy, carboxymethyl, carboxyethyl, alkyl, alkoxy, alkylamino, aryl, aryl sulfonylalkyl, aryloxy, arylalkoxy, NR5R6, azido, nitro, guanidino, amidino, phosphono, oxo, carbamoyl, alkylsulfonyl, alkylsulfinyl, alkylthio, or $SF_5$, and two Y groups can optionally form a methylenedioxy;

R5 and R6 are independently hydrogen, alkyl, aryl, arylalkyl, heteroaryl, or heteroarylalkyl;

wherein alkyl, aryl and heteroaryl groups can be independently optionally substituted by one or more substituents Y; or R5 and R6 together can optionally constitute a heterocycle; or R2 and R3 can constitute a cycle which compound then corresponds to formula (II),

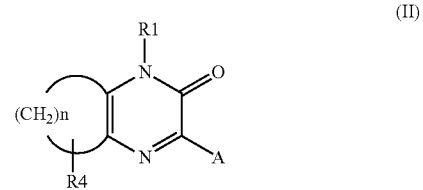

(II)

wherein:
n is 4; and
R4 is one or more hydrogen, alkyl, alkoxy, cycloalkyl, or aryl;
wherein alkyl, cycloalkyl and aryl groups can be optionally substituted by one or more of hydroxy, halogen, alkyl, alkoxy, trifluoromethoxy, trifluoromethyl, or alkylsulfonyl;
or racemic forms, tautomers, enantiomers, diastereomers, epimers, or mixtures thereof, or pharmaceutically acceptable salts thereof.

9. The method according to claim 1, wherein said host suffers from diabetes.

10. The method according to claim 9, wherein said diabetes is type II diabetes.

11. The method according to claim 1, wherein said host suffers from dyslipidemia or obesity.

12. The method according to claim 1, wherein said host suffers from diabetes related microvascular or macrovascular complications.

13. The method according to claim 1, wherein hyperglycemia is reduced in said host.

14. The method according to claim 1, wherein the compound is
1-cyclopropyl-3-phenylpyrazin-2(1H)-one;
1-(cyclopropylmethyl)-3-phenylpyrazin-2(1H)-one;
1-ethyl-3-(4-fluorophenyl)pyrazin-2(1H)-one;
1-ethyl-3-(4-methoxyphenyl)pyrazin-2(1H)-one;
1-ethyl-3-(4-methylphenyl)pyrazin-2(1H)-one;
1-ethyl-3-(5-fluoro-2-methoxyphenyl)pyrazin-2(1H)-one;
1-ethyl-3-[4-(methylsulfonyl)phenyl]pyrazin-2(1H)-one;
1-ethyl-3-[4-(trifluoromethoxy)phenyl]pyrazin-2(1H)-one;
1-ethyl-3-[4-(trifluoromethyl)phenyl]pyrazin-2(1H)-one;
1-ethyl-3-phenylpyrazin-2(1H)-one;
1-ethyl-3-(1H-indol-5-yl)pyrazin-2(1H)-one;
1-ethyl-3-(1H-indol-6-yl)pyrazin-2(1H)-one;
1-ethyl-3-quinolin-6-ylpyrazin-2(1H)-one;
1-isopropyl-3-phenylpyrazin-2(1H)-one;
1-butyl-3-phenylpyrazin-2(1H)-one;
1-isobutyl-3-phenylpyrazin-2(1H)-one;
3-(1,3-benzodioxol-5-yl)-1-ethylpyrazin-2(1H)-one;
3-(2-ethoxyphenyl)-1-ethylpyrazin-2(1H)-one;

3-(4-chlorophenyl)-1-(cyclopropylmethyl)pyrazin-2(1H)-one;
3-(4-chlorophenyl)-1-ethyl-5,6,7,8-tetrahydroquinoxalin-2(1H)-one;
3-(4-chlorophenyl)-1-ethylpyrazin-2(1H)-one;
3-(4-chlorophenyl)-1-isobutylpyrazin-2(1H)-one;
3-(4-tert-butylphenyl)-1-ethylpyrazin-2(1H)-one;
3-phenyl-1-propylpyrazin-2(1H)-one; or
4-(4-ethyl-3-oxo-3,4-dihydropyrazin-2-yl)benzoic acid;
or racemic forms, tautomers, enantiomers, diastereomers, epimers, or mixtures thereof,
or pharmaceutically acceptable salts thereof.

15. The method according to claim 14, wherein the compound is 3-(1,3-benzodioxol-5-yl)-1-ethylpyrazin-2(1H)-one;
3-(4-chlorophenyl)-1-(cyclopropylmethyl)pyrazin-2(1H)-one;
3-(4-chlorophenyl)-1-ethyl-5,6,7,8-tetrahydroquinoxalin-2(1H)-one;
3-(4-chlorophenyl)-1-isobutylpyrazin-2(1H)-one; or
3-phenyl-1-propylpyrazin-2(1H)-one; or racemic forms, tautomers, enantiomers, diastereomers, epimers, or mixtures thereof, or pharmaceutically acceptable salts thereof.

\* \* \* \* \*

UNITED STATES PATENT AND TRADEMARK OFFICE
CERTIFICATE OF CORRECTION

Page 1 of 1

PATENT NO. : 9,233,937 B2
APPLICATION NO. : 14/337796
DATED : January 12, 2016
INVENTOR(S) : Botton et al.

It is certified that error appears in the above-identified patent and that said Letters Patent is hereby corrected as shown below:

Claims

Column 27, line 61, claim 1 reads "A is selected aryl, heteroaryl, or arylalkyl," this line should be deleted in its entirety.

Column 28, line 26, claim 1 reads "or R2 and R3 can constitute a cycle compound then corre-" should read -- or R2 and R3 can constitute a cycle which compound then corre- --

Signed and Sealed this
Twenty-sixth Day of April, 2016

Michelle K. Lee
*Director of the United States Patent and Trademark Office*